(12) United States Patent
Martin

(10) Patent No.: US 9,956,448 B2
(45) Date of Patent: May 1, 2018

(54) PERFLUOROALKYL COMPOSITION WITH REDUCED CHAIN LENGTH

(71) Applicant: Tyco Fire Products LP, Lansdale, PA (US)

(72) Inventor: Thomas Joseph Martin, Mansfield, TX (US)

(73) Assignee: TYCO FIRE PRODUCTS LP, Lansdale, PA (US)

( * ) Notice: Subject to any disclaimer, the term of this patent is extended or adjusted under 35 U.S.C. 154(b) by 233 days.

(21) Appl. No.: 14/776,057

(22) PCT Filed: Mar. 14, 2014

(86) PCT No.: PCT/US2014/029622
§ 371 (c)(1),
(2) Date: Sep. 14, 2015

(87) PCT Pub. No.: WO2014/144988
PCT Pub. Date: Sep. 18, 2014

(65) Prior Publication Data
US 2016/0023033 A1  Jan. 28, 2016

Related U.S. Application Data

(60) Provisional application No. 61/798,542, filed on Mar. 15, 2013.

(51) Int. Cl.
| | | |
|---|---|---|
| A62D 1/02 | (2006.01) | |
| A62D 1/00 | (2006.01) | |
| C07C 323/22 | (2006.01) | |
| C08G 75/02 | (2016.01) | |

(52) U.S. Cl.
CPC ......... *A62D 1/0085* (2013.01); *A62D 1/0042* (2013.01); *C07C 323/22* (2013.01); *C08G 75/02* (2013.01)

(58) Field of Classification Search
CPC .......................... A62D 1/0071; A62D 1/0085
See application file for complete search history.

(56) References Cited

FOREIGN PATENT DOCUMENTS

| | | |
|---|---|---|
| DE | 195 19 534 A1 | 11/1996 |
| EP | 2 246 324 A1 | 11/2010 |
| WO | WO 01/30873 A1 | 5/2001 |
| WO | WO 2012/045080 A1 | 4/2012 |

OTHER PUBLICATIONS

International Search Report and Written Opinion, International Application No. PCT/US2014/029622 (published as WO 2014/144988) dated Sep. 25, 2014.

*Primary Examiner* — Peter F Godenschwager
(74) *Attorney, Agent, or Firm* — Perkins Coie LLP

(57) ABSTRACT

Novel fluorosurfactants are provided that contain perfluoroalkyl groups no longer than perfluorohexyl ($C_6$). The surfactants are useful in the preparation of aqueous film forming foams (AFFF) and alcohol-resistant film-forming foams (AR-AFFF) for firefighting. Unexpectedly, these compounds have activity in AFFF and AR-AFFF applications that is comparable and even superior to conventional surfactants that contain perfluoroalkyl groups that are perfluorooctyl ($C_8$) and longer. Also provided are methods of making the novel surfactants, as well as foam concentrates, methods of making foam and methods of fighting fires using foam containing the novel surfactants.

24 Claims, 4 Drawing Sheets

PERFLUOROALKYL COMPOSITION WITH REDUCED CHAIN LENGTH

PRIORITY DATA

This application is a 35 U.S.C. § 371 application of International Application No. PCT/US2014/029622, filed Mar. 14, 2014, which claims the benefit of U.S. Provisional Patent Application No. 61/798,542, filed Mar. 15, 2013, each of which application is incorporated herein by reference in its entirety.

BACKGROUND

Firefighting foam concentrates contain mixtures of surfactants that act as foaming agents, together with solvents and other additives that provide the desired mechanical and chemical properties for the foam. The concentrates are mixed with water in situ and foamed by mechanical means, and the resulting foam is projected onto the fire, typically onto the surface of a burning liquid. The concentrates are typically used at a concentration of about 1-6%.

Aqueous film-forming foam (AFFF) concentrates are designed to spread an aqueous film on the surface of hydrocarbon liquids, which increases the rate at which the fire can be extinguished. This spreading property is made possible by the use of perfluoroalkyl surfactants in AFFF, which produce very low surface tension values in solution (15-20 dynes $cm^{-1}$), thereby permitting the aqueous solution to spread on the surface of the hydrocarbon liquids.

However, typical AFFF foams are not effective on fires caused by water-miscible fuels, such as low molecular weight alcohols, ketones, and esters and the like, because the miscibility of the solvent leads to dissolution and destruction of the foam by the fuel. To address this issue, alcohol resistant AFFF (AR-AFFF) concentrates are used, which contain a water-soluble polymer that precipitates on contact with a water-miscible fuel, creating a protective layer between the fuel and the foam. Typical water-soluble polymers used in AR-AFF are polysaccharides, such as xanthan gums. AR-AFFF foams are effective on both hydrocarbon and water-soluble fuels.

Conventional AFFF concentrates contain mixtures of perfluoroalkyl and non-fluorinated surfactants, each of which may be anionic, cationic, nonionic or amphoteric, solvents such as glycols and/or glycol ethers, and minor additives such as chelating agents, pH buffers, corrosion inhibitors and the like. Various AFFF concentrates are described in, for example, U.S. Pat. Nos. 3,047,619; 3,257,407; 3,258,423; 3,562,156; 3,621,059; 3,655,555; 3,661,776; 3,677,347; 3,759,981; 3,772,199; 3,789,265; 3,828,085; 3,839,425; 3,849,315; 3,941,708; 3,95,075; 3,957,657; 3,957,658; 3,963,776; 4,038,198; 4,042,522; 4,049,556; 4,060,132; 4,060,489; 4,069,158; 4,090,976; 4,099,574; 4,149,599; 4,203,850; and 4,209,407. AR-AFFF concentrates are described in, for example, U.S. Pat. No. 4,060,489; U.S. Pat. No. 4,149,599 and U.S. Pat. No. 4,387,032.

Until recently, aqueous film forming foams that were used for fire fighting invariably contained components, including low molecular weight fluorosurfactants and fluoropolymer surfactants having perfluoroalkyl chains where the perfluoroalkyl group was at least a perfluorooctyl ($C_8$) group. For example, it was believed that a surfactant required at least a perfluorooctyl moiety to provide the necessary physicochemical attributes for efficient and persistent foam formation for fire fighting applications. See WO03/049813. However, perfluorooctyl moieties have been shown to be environmentally persistent and to accumulate in the livers of test animals, leading to calls for the phase-out of materials, including foam components, containing a perfluorooctyl group. Recent regulatory efforts such as the United States EPA's PFOA Stewardship Program and EC directives pertaining to telomer-based higher homologue perfluorinated surfactants have sought to discourage use of perfluorooctyl-containing components.

Fluorocarbon surfactant suppliers and formulators have been seeking to replace $C_8$+ perfluoroalkyl chain products with $C_6$ or lower perfluoroalkyl chain products to avoid the potential for environmental harm due to the persistence of the residual fluorinated alkyl chain. Perfluorohexanoic acid (PFHxA), the presumed ultimate decomposition product of $C_6$ fluorocarbon surfactants has been shown to be non-toxic and non-bio-accumulative, however. The EPA and other regulatory authorities therefore prefer the use of $C_6$ over $C_8$ and higher perfluoroalkyl homologs and are actively pursuing regulation of the production and importation of such $C_8$ and higher perfluoroalkyl products.

Although $C_6$ fluorosurfactants have been reported to be satisfactory for less demanding applications, such as cleaning solutions, the reduction in length of the perfluoroalkyl chain unfortunately leads to a decrease in the ability to form long lasting persistent foams with the properties necessary for effective fire fighting. Thus, AFFF and AR-AFFF concentrates where the perfluorooctyl surfactant is replaced by an equivalent $C_6$ compound typically are unable to meet the requirements of the US and international standards for fire fighting applications.

To counter this loss of activity, manufacturers have been forced to increase the concentration of fluorosurfactant in AFFF concentrates and/or to use oligomeric surfactants in which multiple perfluoroalkyl groups are covalently attached to short polymeric carrier molecules. See WO01/030873. In both instances the total concentration of fluorine atoms (calculated on a weight percentage basis) remains at an undesirably high level.

DETAILED DESCRIPTION

Figure 1:
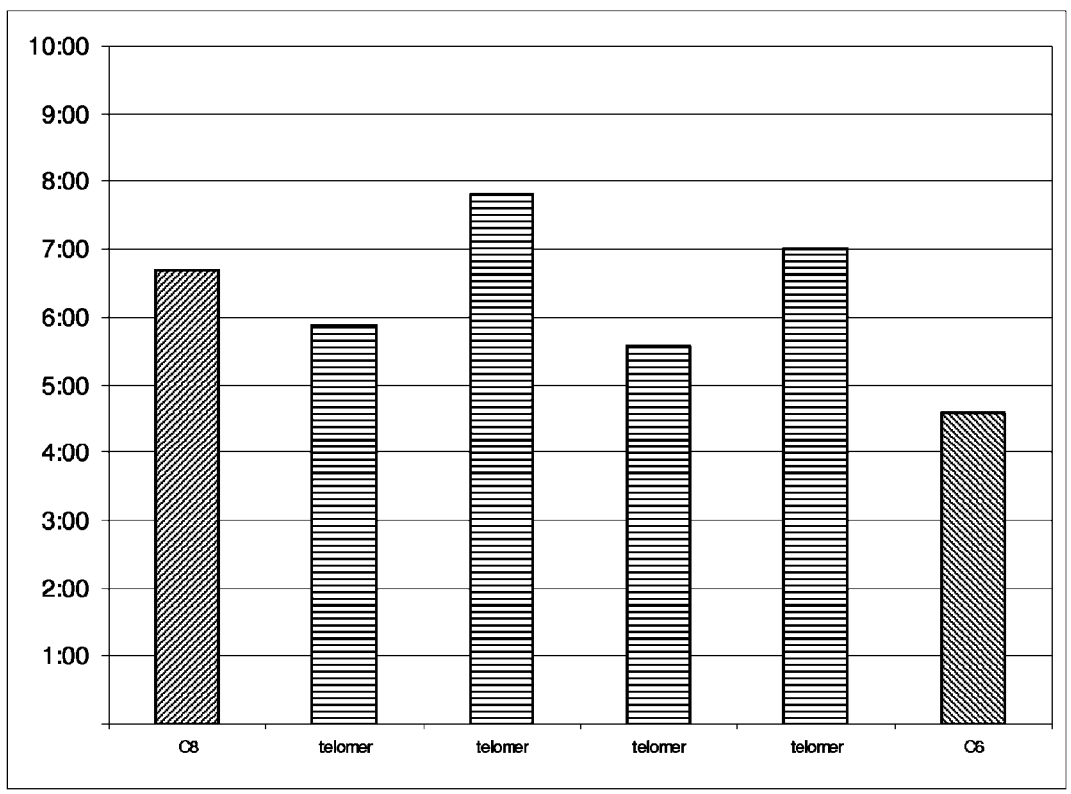
FIG. 1 shows a plot of the performance in sprinkler deluge tests of an extended chain $C_6$ perfluoroalkyl telomer polymer fire fighting foam at different concentrations in comparison to $C_8$ and short chain $C_6$ compounds.

Novel fluorosurfactants are provided that contain perfluoroalkyl groups no longer than perfluorohexyl ($C_6$). The surfactants are useful in the preparation of aqueous film forming foams (AFFF) and alcohol-resistant film-forming foams (AR-AFFF) for firefighting. Unexpectedly, these compounds have activity in AFFF and AR-AFFF applications that is comparable and even superior to conventional surfactants that contains perfluoroalkyl groups that are perfluorooctyl ($C_8$) and longer. Also provided are methods of making the novel surfactants, as well as foam concentrates, methods of making foam and methods of fighting fires using foam containing the novel surfactants.

Unfortunately, until the present time it has not been possible to prepare compositions containing perfluoroalkyl groups that are shorter than perfluorooctyl yet still retain the necessary properties to allow preparation of effective AFFF at the "industrial standard" of fluorine levels. Unexpectedly, it has now been found that certain fluorosurfactants containing $C_4$-$C_6$ perfluoro moieties can be prepared that provide performance that is at least comparable to the performance of equivalent $C_8$ perfluoro moieties in allowing the preparation of AFFF. Moreover, even more unexpectedly, these fluorosurfactants can be used to prepare AFFF concentrates that are still effective even when foamed with water containing a high salt content, e.g. seawater or brackish water.

It has been discovered that highly effective surfactants with shorter perfluoroalkyl moieties can be prepared by replacing difluoromethylene ($—CF_2—$) groups with unsubstituted ($—CH_2—$) groups. Specifically, replacing a single $—CF_2—$ moiety in a surfactant with two or more $—CH_2—$ groups provides a surfactant that has comparable or better activity. Thus, replacing two $—CF_2—$ moieties in a $C_8$ surfactant with at least four $—CH_2—$ groups provides a $C_6$ fluorosurfactant with properties that match or exceed those of the $C_8$ compound.

Most conventional perfluorosurfactants contain mixtures of different perfluoroalkyl chain lengths (typically $C_8$, $C_{10}$, $C_{12}$, etc.) as a result of the telomerization process used in their preparation. The present fluorinated surfactants are essentially free of perfluoroalkyl groups of other chain lengths. Thus, for example, a $C_6$ surfactant is essentially free of $C_8$, $C_{10}$, $C_{12}$ etc.

A typical $C_8$ fluorosurfactant contains a chain of structure $C_8F_{17}—CH_2—CH_2—$. The novel compounds described below can contain perfluoroalkyl moieties of the general structure $CF_3(CF_2)_n—(CH_2)_x—$ or $CHF_2(CF_2)_n—(CH_2)_x—$, where n is 3-5 and x is 6 or more. Methods of making such perfluoroalkyl moieties are known in the art; however, it typically is more convenient to extend the chain length of the non-perfluorinated part of the chain using a heteroatom-containing linker moiety, which allows the use of commercially available starting materials and simplifies the synthesis of the molecule.

Structure of the Surfactants

The $C_4$-$C_6$ surfactants have the structure I

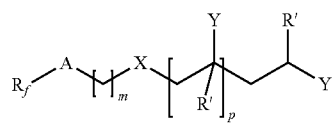

where $R_f$ is $CF_3(CF_2)_n—$ or $CHF_2(CF_2)_n—$, and where n is 3-5. A is a linker that can be $—CH_2CH_2—$, $—CH_2CH_2—S—$, $—CH_2CH_2—O—$, $—CH_2CH_2—CO—NH—$, $—CH_2CH_2—NH—CO—$, $—CH_2CH_2—SO_2NH—$, $—CH_2CH_2—NHSO_2—$, $—CH_2CH_2—OC(O)—$, $—CH_2CH_2—C(O)O—$, $—CH_2CH_2—S(O)—$, or $—CH_2CH_2—SO_2—$. Advantageously, $R_f$ is $C_6F_{13}—$ and A is $—CH_2CH_2—S—$. The length of the methylene chain between A and X can be $C_2$-$C_8$, that is, m can be 2-8. Advantageously, m is 4.

X can be $—S—$, $—O—$, $—SO_2—$, $—NR—$, $—CO_2—$, $—CONR—$, $—SO_2NR—$, $—OP(O)(OR)O—$, $S(O)$, $—OC(O)—$, $—NRC(O)—$, or $—NRSO_2—$, where R is H or $C_1$-$C_6$ alkyl. Advantageously, X is $—S—$.

Y can be $—CONHR$, $—CO_2H$, $—CO_2R$, $—OC(O)R$, or $—C_6H_4SO_3M$, where R is H or $C_1$-$C_6$ alkyl, and M is a metal ion. R' can be H or $C_1$-$C_6$ alkyl. Advantageously, Y is $CONH_2$ and R' is H. When Y is $—C_6H_4SO_3M$, M advantageously is an alkali metal ion, such as $Na^+$. The sulfonate moiety on $—C_6H_4SO_3M$ can be in the 2-, 3-, or 4-position, but advantageously is in the 4-position.

In a particularly advantageous embodiment, $R_f$ is $C_6F_{13}$, A is $—CH_2CH_2—S—$, m is 4, and X is $—S—$.

Compositions of formula I are prepared by a polymerization reaction as described in more detail below, and therefore the composition will contain molecules with differing values of p, depending on the polymerization conditions chosen and subsequent purification methods. Advantageously, p is 2-100, and typically is 4-20, on average.

These surfactant compositions advantageously are used in compositions that are substantially free of any surfactant containing a perfluoroalkyl group containing more than 6 carbon atoms. In the present context a composition is substantially free of a component when that component is present, if at all, at trace (impurity) levels that are too low to materially affect the properties of the composition.

The weight average molecular weight of the surfactant will vary depending on the nature of Rf, A, m, X, p, R' and Y, but advantageously is 750-7500, although the skilled artisan will recognize that molecular weights above and below this range can be used.

In a specific embodiment, the said surfactant has the formula

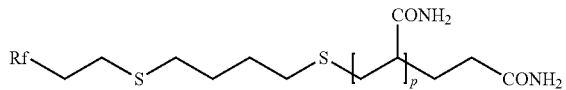

where p is 2-100, 2-50, 4-50 or 4-20.

Synthesis of the Surfactants

The surfactants can be prepared using methods that are well known in the art of organic synthesis and polymer synthesis. Broadly speaking, the linker A is formed using well-known alkylation or acylation reaction from commercially available starting materials, and the resulting compound is used in a polymerization reaction with an acrylic acid or styrene derivative.

For example, when A is $—CH_2CH_2—S—$, and X is also S, then perfluorohexyl ethyl thiol can be reacted with an excess of dichlorobutane, catalyzed with triethylamine. After the reaction is complete, the excess dichlorobutane is removed by evaporation, providing $R_fCH_2CH_2S(CH_2)_4Cl$. This compound is in turn reacted with thiourea, followed by a diamine to convert the chloride into a thiol, providing $R_fCH_2CH_2S(CH_2)_4SH$. The thiol is then reacted with an acrylic acid derivative, styrene, or vinyl ether in the presence of a suitable polymerization initiator.

The acrylic acid derivative has the general structure II

where Y is —CONHR, —OC(O)R, —CO$_2$H, —CO$_2$R or —C$_6$H$_4$SO$_3$M, R' is H or C$_1$-C$_6$ alkyl, and M is a metal ion.

Suitable initiators are well known in the art and include commercially available azo-type and peroxide-type compounds, for example, dicyclohexyl peroxydicarbonate, benzoyl peroxide or di-tert-butyl peroxide. The reaction temperature of the polymerization can be varied as needed and may be between 0° C. and 150° C., though typically the reaction temperature is conveniently set at the reflux temperature of the reaction solvent (such as, for example, t-butanol, isopropyl alcohol or various glycols and glycol ethers) and advantageously is between about 60° C. and 90° C. The resulting polymer has the structure:

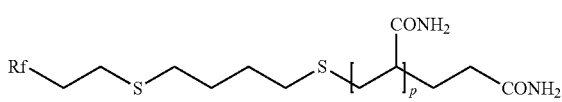

The desired value of p can be varied using well known methods such as, for example, adjusting the stoichiometry of the reagents and the reaction conditions.

Methods of making compounds where the A and X moieties are varied will be apparent to one skilled in the art. For example, the compound where A is —C(O)NH— and X is —NH— can readily be prepared by reaction of R$_f$CH$_2$CH$_2$COCl with NH$_2$(CH$_2$)$_4$NH$_2$ to give R$_f$CH$_2$CH$_2$S(CH$_2$)$_4$NH$_2$, which can then be reacted with, for example, polyacrylamide, to give the desired polymer. One of ordinary skill in the art will appreciate that the other combinations of A and X can all be prepared in similarly straightforward fashion using well known and conventional organic chemical reactions, such as alkylation, acylation, sulfonylation, etc. of a nucleophilic thiol, amine, or alcohol, as required.

Compositions Containing the Fluoropolymers

The fluorosurfactant as described above can be used to prepare aqueous firefighting composition concentrates that are effective for preparing aqueous film-forming foams, including alcohol-resistant aqueous film-forming foams. Specifically, the fluoropolymer can be used to prepare AFFF and AR-AFFF concentrates where the concentrate composition is substantially free of any surfactant containing a perfluoroalkyl group containing more than 6 carbon atoms. AFFF and AR-AFFF concentrates containing fluorosurfactants are known in the art and the fluorosurfactant described herein can be used to replace some or all of the fluorosurfactant used in the concentrates known in the art. See for example, U.S. Pat. No. 7,011,763, the contents of which are hereby incorporated by reference in their entirety.

Concentrates prepared from the fluorosurfactants described herein are useful for extinguishing UL162 Class B polar (water soluble) and non-polar (water insoluble) liquid fuel fires. The concentrates also meet the standards set forth in EN 1568-3 and EN 1568-4. Methods for determining the effective amount of fluoropolymer for use in the concentrates are well known in the art.

The AFFF and AR-AFFF concentrates may be produced at any suitable strength, including, but not limited to, 1, 3 and 6% (w/w) foam concentrates, which are concentrations that are typical for commercial use. Concentrates that are less than 1% (w/w) or greater than 6% (w/w) also may be prepared. As used herein, the lowest numbered strength for the concentrate used indicates the most concentrated product, i.e., the percent designation refers to the proportioning rate of foam concentrate to water. Accordingly, one part of 1% concentrate used with 99 parts water gives 100 parts of use strength pre-mix; similarly, three parts 3% concentrate and 97 parts water gives 100 parts of pre-mix. As used herein, the term "water" may include pure, deionized or distilled water, tap or fresh water, sea water, brine, or an aqueous or water-containing solution or mixture capable of serving as a water component for the fire fighting composition.

Typical components used for preparing AFFF concentrates are shown in the table below, together with typical % concentrations (w/w).

| Component | % by weight |
|---|---|
| C$_6$ Fluorosurfactant | 0.1-2 |
| Electrolytes | 0-3 |
| Zwitterionic alkyl sulfate detergent | 0-3 |
| Anionic hydrocarbon surfactant | 2-10 |
| Glycol ether | 0-15 |
| Nonionic surfactant | 0-5 |
| Fluorosurfactant | 0-1 |
| Water | balance |

Typical components used for preparing AR-AFFF concentrates are shown in the table below, together with typical % concentrations (w/w).

| Component | % by weight |
|---|---|
| High MW fluorinated polymer (HMW-FP) | 0.2-10 |
| Amphoteric Hydrocarbon Surfactant | 0-3 |
| Anionic Hydrocarbon Surfactant | 2-10 |
| Nonionic Hydrocarbon surfactant | 0-5 |
| Fluorochemical Surfactant | 0.1-2 |
| Foam aids including glycol ethers | 0-15 |
| Freeze protection package | 0-45 |
| Sequestering, buffer, corrosion package | 0-5 |
| Polymeric film formers | 0-2 |
| Biocides, antimicrobial | 0-0.1 |
| Electrolytes | 0-3 |
| Polymeric foam stabilizers and thickeners | 0-10 |
| Water | Balance |

The above components would be reduced or increased accordingly relative to the 3% liquid concentrate to prepare 6% and 1% synthetic liquid foam concentrates, or other concentrate levels. Thus, for a 1% concentrate, the above amounts may be increased by a factor of 3, whereas for a 6% concentrate the above amounts may be reduced by half.

Typical components for foam concentrates include:

C$_6$ Fluorosurfactant Component

The C$_6$ surfactants as described herein may be used in an AFFF or AR-AFFF concentrate in an effective amount to provide the desired foam properties. Typical wt % ranges for the surfactant are 0.1-4%, advantageously 0.1-2%, although higher amounts may be used if desired.

Hydrocarbon Surfactants

Amphoteric hydrocarbon surfactants include, but are not limited to, those which contain, in the same molecule, amino and carboxy, sulfonic, and sulfuric ester moieties and the like. Higher alkyl (C$_6$-C$_{14}$) betaines and sulfobetaines are included in this category. Commercially available products include Chembetaine CAS (Lubrizol Inc.) and Mirataine CS (Rhodia), both sulfobetaines, and Deriphat 160C (BASF), a C$_{12}$ amino-dicarboxylate. These products are foaming agents and help reduce interfacial tension in water solution.

Anionic hydrocarbon surfactants include, but are not limited to, alkyl carboxylates, sulfates, sulfonates, and their ethoxylated derivatives. Alkali metal and ammonium salts are suitable. $C_8$-$C_{16}$ hydrocarbon surfactants are suitable, including, advantageously, $C_8$-$C_{10}$.

Nonionic hydrocarbon surfactants help reduce interfacial tension and solubilize other components, especially in hard water, sea water or brine solutions. They also serve to control foam drainage, foam fluidity, and foam expansion. Suitable nonionic surfactants include, but are not limited to, polyoxyethylene derivatives of alkylphenols, linear or branched alcohols, fatty acids, alkylamines, alkylamides, and acetylenic glycols, alkyl glycosides and polyglycosides, as defined in U.S. Pat. No. 5,207,932 (herein incorporated by reference) and others, and block polymers of polyoxyethylene and polyoxypropylene units.

Other Fluorocarbon Surfactants

Fluorochemical surfactants are typically single perfluorotail molecules and may have multiple hydrophilic heads. Advantageously, the fluorochemical surfactant contains perfluoroalkyl groups no longer than $C_6$, although $C_8$ and longer fluorosurfactants can also be used. Examples of suitable fluorochemical surfactants include those described in WO/2012/045080.

Foam Aids

Foam aids may be used to enhance foam expansion and drain properties, while providing solubilization and antifreeze action. Useful foam aids are well known in the art and are disclosed, for example, in U.S. Pat. Nos. 5,616,273; 3,457,172; 3,422,011 and 3,579,446, which are herein incorporated by reference.

Typical foam aids include alcohols or ethers such as ethylene glycol monoalkyl ethers, diethylene glycol monoalkyl ethers, propylene glycol monoalkyl ethers, dipropylene glycol monoalkyl ethers, triethylene glycol monoalkyl ethers, 1-butoxyethoxy-2-propanol, glycerine, and hexylene glycol.

Freeze Protection Package

The freeze protection package is used to prevent the concentrate freezing or becoming unusably viscous at low temperatures. Typical components include glycerine, ethylene glycol, diethylene glycol, and propylene glycol. Other potential components include salts and other solids which reduce the freezing point of the concentrate, such as calcium, potassium, sodium and ammonium chloride and urea.

Sequestering, Buffer, and Corrosion Package

The components of the sequestering, buffer, and corrosion package, include agents that sequester and chelate metal ions. Examples include polyaminopolycarboxylic acids, ethylenediaminetetraacetic acid, citric acid, tartaric acid, nitrilotriacetic acid, hydroxyethylethylenediaminetriacetic acid and salts thereof. Buffers are exemplified by Sorensen's phosphate or McIlvaine's citrate buffers. The nature of the corrosion inhibitors is limited only by compatibility with other formula components. Typical corrosion inhibitors include ortho-phenylphenol, toluyl triazole, and many phosphate ester acids.

Polymeric Film Former

These water-soluble polymeric film formers, dissolved in AR-AFFF agents, precipitate from solution when the bubbles contact polar solvents and fuel, and form a vapor-repelling polymer film at the solvent/foam interface, preventing further foam collapse. Examples of suitable compounds include thixotropic polysaccharide gums as described in U.S. Pat. Nos. 3,957,657; 4,060,132; 4,060,489; 4,306,979; 4,387,032; 4,420,434; 4,424,133; 4,464,267, 5,218,021, and 5,750,043, which are herein incorporated by reference. Suitable commercially available compounds are marketed as Rhodopol, Kelco, Keltrol, Actigum, Cecal-gum, Galaxy, and Kelzan.

Gums and resins useful as film formers include acidic gums such as xanthan gum, pectic acid, alginic acid, agar, carrageenan gum, rhamsan gum, welan gum, mannan gum, locust bean gum, galactomannan gum, pectin, starch, bacterial alginic acid, succinoglucan, gum arabic, carboxymethylcellulose, heparin, phosphoric acid polysaccharide gums, dextran sulfate, dermantan sulfate, fucan sulfate, gum karaya, gum tragacanth and sulfated locust bean gum.

Neutral polysaccharides useful as film formers include: cellulose, hydroxyethyl cellulose, dextran and modified dextrans, neutral glucans, hydroxypropyl cellulose, as well, as other cellulose ethers and esters. Modified starches include starch esters, ethers, oxidized starches, and enzymatically digested starches.

Antimicrobials and Preservatives

These components may be used to prevent biological decomposition of natural product based polymers incorporated as polymeric film formers. Examples include Kathon CG/ICP (Rohm & Haas Company) and Givgard G-4 40 (Givaudan, Inc.), and are disclosed in U.S. Pat. No. 5,207,932, which is herein incorporated by reference. Additional preservatives are disclosed in U.S. Pat. Nos. 3,957,657; 4,060,132; 4,060,489; 4,306,979; 4,387,032; 4,420,434; 4,424,133; 4,464,267, 5,218,021, and 5,750,043.

Electrolytes

Electrolytes may be added to AFFF and AR-AFFF agents to balance the performance of such agents when proportioned with water ranging from soft to very hard, including sea water or brine, and to improve agent performance in very soft water. Typical electrolytes include salts of monovalent or polyvalent metals of Groups 1, 2, or 3, or organic bases. The alkali metals particularly useful are sodium, potassium, and lithium, or the alkaline earth metals, especially magnesium, calcium, strontium, and zinc or aluminum. Organic bases might include ammonium, trialkylammonium, bis-ammonium salts or the like. The anions of the electrolyte are not critical, except that halides may not be desirable due to metal corrosion. Sulfates, bisulfates, phosphates, nitrates and the like are commonly used. Examples of polyvalent salts include magnesium sulfate and magnesium nitrate.

Polymeric Foam Stabilizers and Thickeners

Polymeric foam stabilizers and thickeners may be included if desired. These components can be optionally incorporated to enhance the foam stability and foam drainage properties. Examples of polymeric stabilizers and thickeners include partially hydrolyzed protein, starches, polyvinyl resins such as polyvinyl alcohol, polyacrylamides, carboxyvinyl polymers, polyvinyl polypyrrolidone, and poly(oxyethylene)glycol.

$C_6$ fluorosurfactants as described herein may be used with commercially available synthetic surfactant concentrates to prepare foam concentrates. The commercially available surfactant concentrates are marketed worldwide and include those available from Chemguard, Kidde, and Tyco. These products include: Class A foams (CLASS A PLUS and SILVEX), excellent for extinguishing forest fires, structural fires, and tire fires; high expansion foams sold under the names HI-EX, EXTRA, C2, and VEE-FOAM; vapor suppressant foam sold by Chemguard as VRC foam; bomb foam, a 6% product sold by Chemguard as AFC-380.

Synthetic surfactant concentrates listed as "wetting agents" by Underwriters Laboratory may also be included as base surfactant mixtures for preparing AR-AFFF concentrates. Products listed by UL as "wetting agents" are as follows: Fire Strike by Biocenter Inc.; Bio-Fire by Envirorenu Technologies LLC; Enviro-Skin 1% by Environmental Products Inc.; F-500 by Hazard Control Technologies Inc.; Knockdown by National Foam Inc.; Phos-Chek WD881 by Solutia Inc.; Flameout by Summit Environmental Corp. Inc. Micro-Blazeout by Verde Environmental Inc.; Bio-solve by Westford Chemical Corp.

Use of Concentrates

Concentrates prepared as described above may be mixed with water, typically as a 3% solution, and foamed using foaming devices well known in the art. As water under pressure passes through a fire hose, typically 3 percent by volume of the concentrate composition is inducted into the hose line by the Venturi effect to form a foam solution of the concentrate diluted with water. The solution becomes aerated to produce a finished foam by use of an air-aspirating nozzle located at the outlet end of the hose. A foam solution stored for any length of time prior to aeration is known as a foam premix and can likewise be aerated to produce a finished foam. Equipment which can be used to produce and apply these aqueous air-foams are known in the art and also are described in publications by the National Fire Protection Association.

The concentrate, upon dilution with water and aeration, produces an aqueous film-forming foam which is applied to a body of flammable liquid such as a spill or pool which is burning or subject to ignition. The foam extinguishes the burning liquid, and prevents further ignition by providing a blanket to cover the fuel surface and excluding air.

Preferably, the compositions are introduced into a fire or flame in an amount sufficient to extinguish the fire or flame. One skilled in the art will recognize that the amount of extinguishing composition needed to extinguish a particular hazard will depend upon the nature and extent of the hazard.

The following examples serve to further illustrate the invention.

EXAMPLES

Example 1: Exemplary Fluorosurfactants Synthesis 1,4-Dichlorobutane (27.5 g, 0.22 mol), triethylamine (2.3 g, 0.02 mol) and perfluorohexylethanethiol (8.1 g, 0.02 mol) were heated at 80-90° C. for 3 hours. Aqueous acetic acid was added and the mixture maintained at 70° C. for 30 minutes. The organic layer was separated and evaporated in vacuo to provide $C_6F_{13}(CH_2)_2S(CH_2)_4Cl$, which was used without further purification. The product (8.5 g, 0.017 mol) was heated with thiourea (1.6 g, 0.02 mol) in a mixture of dipropylene glycol and ethylene glycol at 100° C. for 4 hours. Subsequently, isopropanol, water and ethylene diamine (0.6 g, 0.01 mol) were added. The mixture was cooled to 60° C. and mixed for 1 h. The organic layer was separated and treated with acetic acid to obtain the product $C_6F_{13}(CH_2)_2S(CH_2)_4SH$.

Acrylamide (9.2 g, 0.129 mol) was dissolved in tert-butanol at 30-35° C. in the presence of a small amount of acetic acid (0.1 ml). The thiol prepared in the prior step was added (4.4 g. 0.008 mol) and the mixture heated under reflux as a free radical initiator was added slowly over 5.5 hours. Solvent was removed by distillation and the pH of the resulting product adjusted to 5.3-6.3 using aqueous sodium hydroxide. The resulting surfactant was used without further purification.

Example 2

The material from Example 1 ("telomer") was formulated into a standard foam concentrate and compared to a conventional $C_8$ perfluoroalkyl surfactant and a conventional (short chain) $C_6$ perfluoroalkyl surfactant. The concentrate contained, in addition to the fluorosurfactants, magnesium sulfate, zwitterionic, nonionic and anionic hydrocarbon surfactants, a glycol ether and water. The telomer was formulated at several different concentrations. The concentrates were then tested on the standard Underwriters Laboratory 162 ("UL 162") test. To pass the test the deluge time must exceed 5 minutes. As shown in FIG. 1, all telomer concentrations passed the test, as did the $C_8$ surfactant, but the short chain $C_6$ surfactant did not meet the five-minute deluge test.

Example 3

Figure 2:
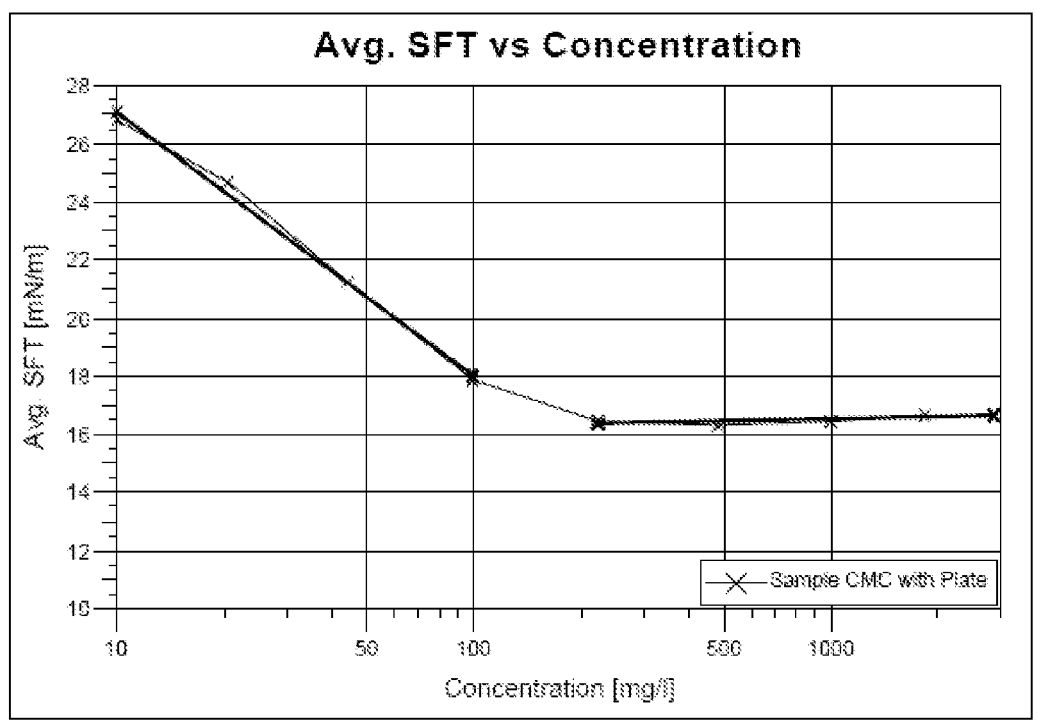
FIG. 2 shows a plot of the average surface tension of an extended chain $C_6$ perfluoroalkyl telomer foam product at different concentrations.

The surface tension of the telomer from Example 1 was measured at various concentrations and the results are shown in FIG. 2. Extended-linking-chain $C_6$ perfluoroalkyl polyacrylamide product described in Example 1 was used at various concentrations and the surface tension of the various concentrations was measured. The sharp inflection point and low ultimate surface tension demonstrate good surfactant properties.

Example 4

Figure 3:
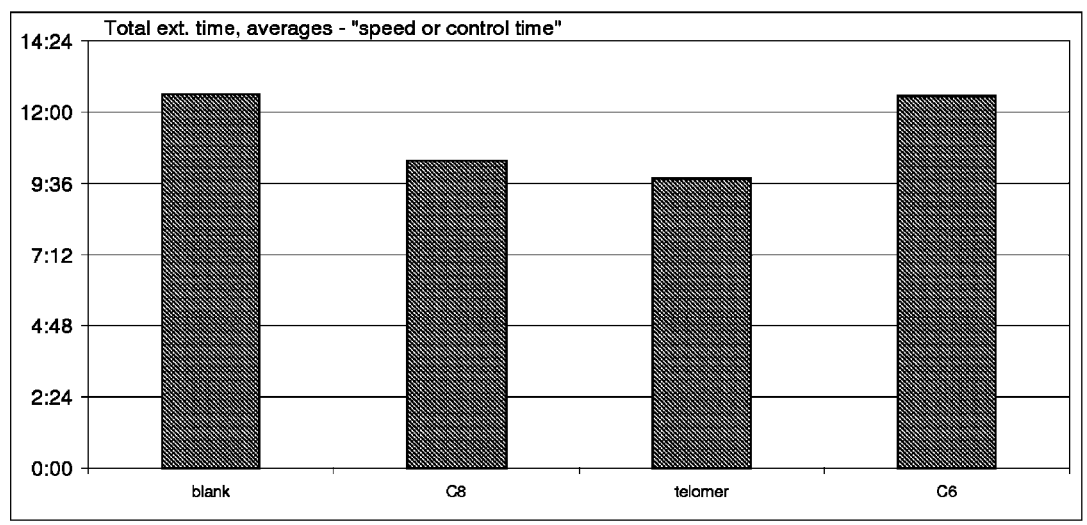
FIG. 3 compares fire control times of an extended chain $C_6$ perfluoroalkyl telomer polymer fire fighting foam in comparison to $C_8$ and short chain $C_6$ compounds.

The telomer from Example 1 was formulated into a standard protein-containing foam base available from National Foam (Exton, Pa.). An extended-linking-chain $C_6$ perfluoroalkyl polymer (telomer) prepared as described in Example 1 was used in a standard fire control test using gasoline as fuel, measuring the time required to extinguish the fire. The result for the telomer was compared to a formulation with no surfactant (blank), and to conventional $C_8$ and short chain $C_6$ surfactants. The results are shown in FIG. 3 and demonstrate the high performance of the telomer Example 5

The formulations used in Example 2 were also tested in UL162 sprinkler tests. In the top plot of FIG. 4, control and extinguishment under five minutes is passing. As shown, all the samples passed.

Figure 4:
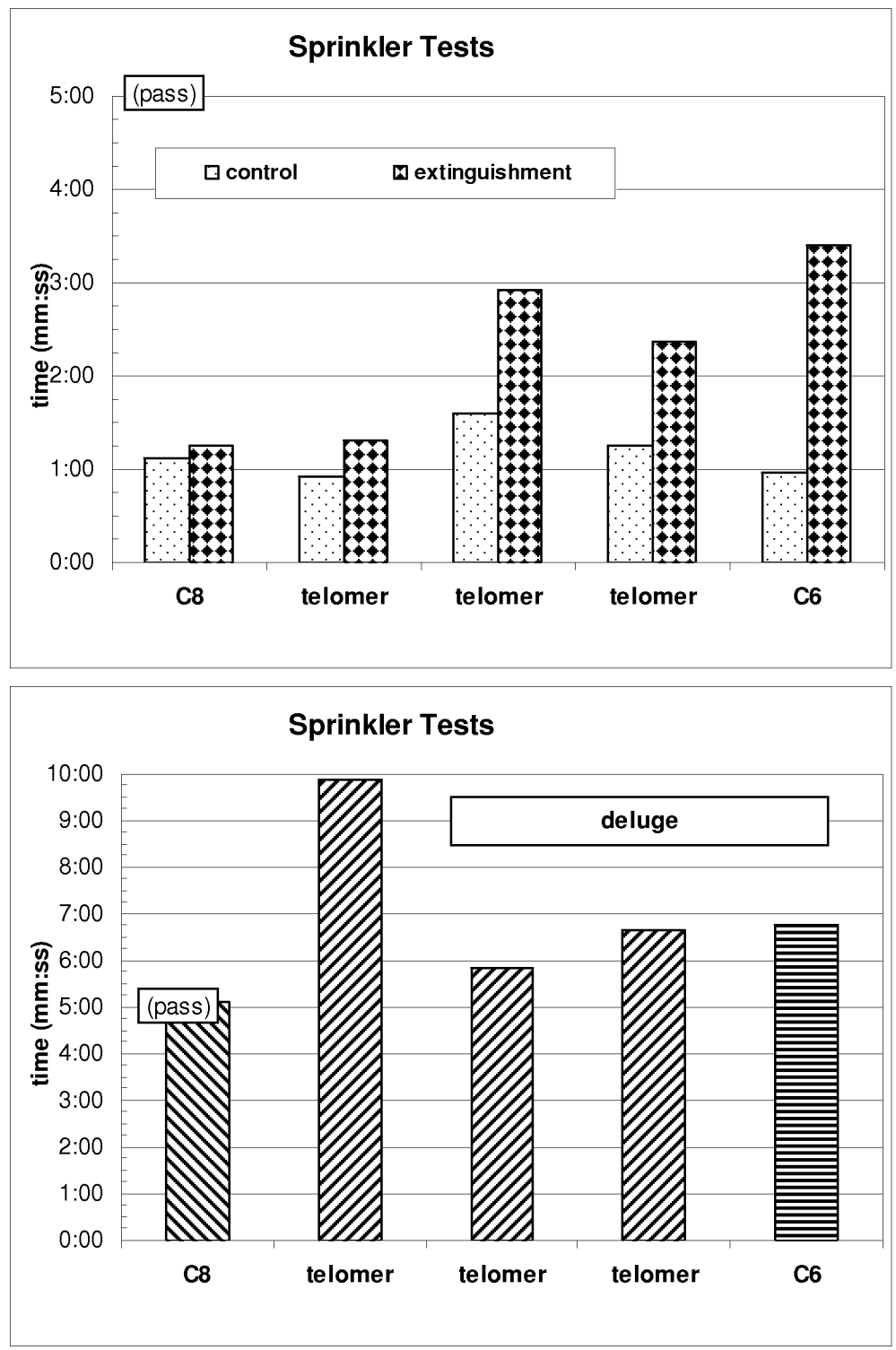
FIG. 4 shows sprinkler (top) and deluge (bottom) test performance of an extended chain $C_6$ perfluoroalkyl telomer polymer fire fighting foam at different concentrations in comparison to $C_8$ and short chain $C_6$ compounds.

In the bottom plot of FIG. 4 the samples were tested in the UL162 deluge test and the length of time that the foam integrity was preserved was measured. An acceptable product maintains its foam integrity for five minutes or more. The results show that the telomer product matched the performance of the $C_8$ and short-chain $C_6$ surfactants when used at the same concentrations (second and third telomer bar) and exceeded that performance when used at 50% excess (first telomer bar).

While the invention has been shown in only some of its forms, it should be apparent to those skilled in the art that it is not so limited, but is susceptible to various changes and modifications without departing from the scope of the invention. Accordingly, it is appropriate that the appended claims be construed broadly and in a manner consistent with the scope of the invention.

The invention claimed is:

1. A fire-fighting foam, comprising a composition comprising a surfactant having the formula

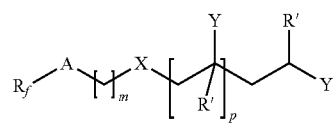

wherein $R_f$ is $CF_3(CF_2)_n$ or $CHF_2(CF_2)_n$, wherein n is 3-5;

A is a linker selected from the group consisting of —$CH_2CH_2$—, —$CH_2CH_2$—S—, —$CH_2CH_2$—O—, —$CH_2CH_2$—CO—NH—, —$CH_2CH_2$—NH—CO—, —$SO_2NH$—, —$NHSO_2$—, —OC(O)—, —C(O)O—, —S(O)—, and —$SO_2$—;

X is selected from the group consisting of —S—, —O—, —$SO_2$—, —NR—, —$CO_2$—, —CONR—, —$SO_2NR$—, —OP(O)(OR)O—, S(O), —OC(O)—, —NRC(O)—, and —$NRSO_2$—;

Y is selected from the group consisting of —CONHR, $CO_2H$, —$CO_2R$, —OC(O)R, and —$C_6H_4SO_3M$;

R is H or $C_1$-$C_6$ alkyl;

R' is H or $C_1$-$C_6$ alkyl;

M is a metal ion; and m is 2-8 and p is 2-100, and wherein said composition is substantially free of any surfactant containing a perfluoroalkyl group containing more than 6 carbon atoms.

2. A method of making a fire-fighting foam, comprising foaming a composition according to claim 1 with an aqueous liquid.

3. A method of fighting a fire comprising contacting a fire with a foam prepared according to the method of claim 2.

4. The method according to claim 2, wherein said aqueous liquid is brackish water or seawater.

5. The fire-fighting foam according to claim 1, wherein said composition further comprises an effective amount of one or more components selected from the group consisting of: an amphoteric hydrocarbon surfactant, an anionic hydrocarbon surfactant, a nonionic hydrocarbon surfactant, a $C_6$ fluorochemical surfactant, a foam aid, a freeze protection composition, a composition comprising ion sequestering, buffer, and anti-corrosion components, a polymeric film forming composition, a biocides and antimicrobial composition, an electrolyte composition, and a polysaccharide gum thickener.

6. The fire-fighting foam according to claim 5, wherein said composition comprises an amphoteric hydrocarbon surfactant in an amount up to 3% w/w.

7. The fire-fighting foam according to claim 5, wherein said composition comprises an anionic hydrocarbon surfactant in an amount of 2-10% w/w.

8. The fire-fighting foam according to claim 5, wherein said composition comprises a nonionic hydrocarbon surfactant in an amount up to 5% w/w.

9. The fire-fighting foam according to claim 5, wherein said composition comprises an additional $C_6$ fluorochemical surfactant in an amount up to 0.4% w/w.

10. The fire-fighting foam according to claim 5, wherein said composition comprises a foam aid in an amount up to 15% w/w.

11. The fire-fighting foam according to claim 1, wherein said composition comprises a freeze protection composition in an amount up to 45% w/w.

12. The fire-fighting foam according to claim 1, wherein said composition comprises ion sequestering, buffer, and anti-corrosion components in an amount up to 5% w/w.

13. The fire-fighting foam according to claim 1, wherein said composition comprises a polymeric film forming composition in an amount up to 2%.

14. The fire-fighting foam according to claim 1, wherein said composition comprises biocides and/or antimicrobials in an amount up to 0.1% w/w.

15. The fire-fighting foam according to claim 1, wherein said composition comprises electrolytes in an amount up to 3% w/w.

16. The fire-fighting foam according to claim 1, wherein said composition comprises at least one polysaccharide gum thickener in an amount up to 10% w/w.

17. The fire-fighting foam according to claim 1, comprising magnesium sulfate.

18. The fire-fighting foam according to claim 1, wherein $R_f$ is $CF_3(CF_2)_5$.

19. The fire-fighting foam according to claim 1, wherein A is —$CH_2CH_2$—S—.

20. The fire-fighting foam according to claim 1, wherein m is 4.

21. The fire-fighting foam according to claim 1, wherein X is —S—.

22. The fire-fighting foam according to claim 1, wherein the weight average molecular weight of said surfactant is 750-7500.

23. The fire-fighting foam according to claim 1, wherein the surfactant has the formula

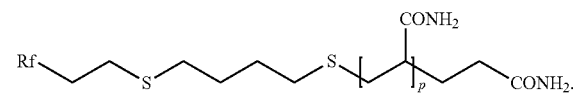

24. The fire-fighting foam according to claim 1, wherein p is 4-20.

* * * * *